United States Patent [19]

Obayashi et al.

[11] Patent Number: 4,668,631

[45] Date of Patent: May 26, 1987

[54] PROCESS FOR PRODUCING A RESTRICTION ENZYME

[75] Inventors: Akira Obayashi, Uji; Nobutsugu Hiraoka, Mukoo; Keiko Kita, Kyoto; Hiroshi Nakajima, Ootsu, all of Japan

[73] Assignee: Takara Shuzo Co., Ltd., Kyoto, Japan

[21] Appl. No.: 777,674

[22] Filed: Sep. 19, 1985

[30] Foreign Application Priority Data

Sep. 27, 1984 [JP] Japan .................... 59-202199

[51] Int. Cl.$^4$ .......................... C12N 9/22; C12R 1/01
[52] U.S. Cl. .................................. 435/199; 435/822
[58] Field of Search ......................................... 435/199

[56] References Cited

U.S. PATENT DOCUMENTS 4,542,099  9/1985  Sakurai et al. .................. 435/199

OTHER PUBLICATIONS

Nucleic Acids Research, vol. 11, No. 1, r135 to r167, (1983).

*Primary Examiner*—Lionel M. Shapiro
*Attorney, Agent, or Firm*—Wenderoth, Lind & Ponack

[57] ABSTRACT

A restriction endonuclease having the ability to recognize the same base sequence and cleavage sites as SacII and SstII can be produced from Gluconobacter and isolated in pure form because no other restriction enzyme is formed.

1 Claim, No Drawings

PROCESS FOR PRODUCING A RESTRICTION ENZYME

This invention relates to a process for producing a restriction enzyme. More particularly, it relates to a process for producing a restriction enzyme formed by microorganisms belonging to the genus Gluconobacter.

Restriction enzymes are endonucleases that are capable of recognizing a specific sequence of bases on a deoxyribonucleic acid (DNA) molecule and of cleaving the double-stranded DNA chain at specific sites. As a result of recent progress in molecular genetics, biochemistry and related sciences, it is now clear that DNA is the carrier of genetic information, and restriction endonucleases have been extensively used for various purposes (clarification of genetic diseases, mass production of genetic materials based on genetic engineering, etc.). About 100 kinds of endonucleases have so far been isolated from many microorganisms, each being identified by the specific base sequence it recognizes and by the pattern of cleavage.

Of these, Sac II produced by *Streptomyces achromogenes* (ATCC 12767) and Sst II produced by *Streptomyces stanford* [(Nucleic Acids Res., Vol. 11, r135 (1983)], are known as restriction endonucleases which recognize the base sequence as shown below and cleave the DNA chain at the arrow-marked positions.

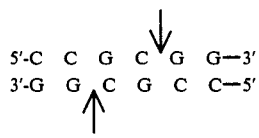

(wherein C represents cytidine, and G guanosine).

Sac II and Sst II, however, have problems for their industrial application. These include their low production yield from the corresponding microorganisms, and unavoidable contamination with Sac I and Sst I, respectively.

The object of this invention is to provide a process for industrial production of a restriction endonulease having the same recognition base sequence and cleavage sites as Sac II and Sst II.

Thus this invention relates to a process for producing a restriction endonuclease capable of specifically cleaving a DNA chain at the arrow-marked positions as shown below, which comprises growing a microorganism belonging to the genus Gluconobacter and capable of producing said enzyme, and collecting the enzyme thus formed from the culture broth,

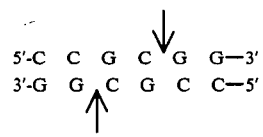

(wherein C represents cytidine, and G guanosine).

We have found that this enzyme having the same recognition base sequence and cleavage sites as Sac II and Sst II can be produced by microorganisms belonging to genus Gluconobacter, and that it can be easily isolated in a pure form because no other restriction enzyme is formed.

Any species of Gluconobacter that are capable of producing this enzyme may be used for the purpose of this invention. Typical examples are *Gluconobacter albidus* IFO 3251 and *Gluconobacter cerinus* IFO 3262 (both stocked at the Institute for Fermentation, Osaka).

For cultivation of these microorganisms, any culture medium may be used if it contains a proper combination of carbon sources, nitrogen sources, inorganic salts and other nutrients assimilable by the microorganism employed. The preferred pH of the medum is in the range from 3.5 to 8.0. Any of the shaking culture, agitation culture and aeration culture methods may be used, but culture with aeration and agitation is most preferable for mass production. Cultivation may be carried out at any temperature that allows formation of this enzyme, but preferred range is from 20° to 30° C. Cultivating time varies with other conditions; cultivation should be continued until a maximum output of this enzyme is achieved.

This enzyme is accumulated principally inside bacterial cells, which can be separated from the culture broth, for example, by centrifugation.

This enzyme can be extracted and purified by using known techniques commonly employed for restriction endonucleases. The collected microbial cells are dispersed in a suitable buffer, and then broken down by ultrasonic treatment to allow extraction of the endonuclease by the buffer solution. After removal of the residue by ultracentrifugation, ammonium sulfate was added to the supernatant for salting out, and the precipitate which separated out was dissolved in a potassium phosphate buffer (pH: 7.5) and dialyzed against a buffer of the same composition. The dialyzate was purified by ion-exchange chromatography on DEAE-cellulose, and by affinity chromatography on Affi-Gel Blue agarose and heparin-Sepharose, giving the endonuclease of this invention.

The activity of this enzyme was determined by the method described below. A substrate solution of the composition shown in Table 1 was prepared.

TABLE 1

| 10 mM | Tris-HCl, pH:8.0 |
| 7 mM | $MgCl_2$ |
| 7 mM | 2-Mercaptoethanol |
| 0.01% | Bovine serum albumin |
| 1.0 μg | λ-DNA (product of Takara Shuzo, Co., Ltd.) |

This substrate solution (50 μl) was preheated to 37° C., the endonuclease of this invention to be tested was added to allow the enzymatic reaction to proceed at that temperature, and the reaction was stopped 60 minutes later by addition of a terminator solution (1% SDS, 50% glycerol, 0.02% Bromophenol Blue). The reaction mixture was applied to a 1% agarose slab gel, and electrophoresis was conducted at a constant voltage of 10 V/cm for one to two hours. The buffer solution used was 90 mM Tris-borate buffer (pH: 8.3) containing 2.5 mM EDTA.

DNA bands can be detected by UV irradiation if 0.5 μg/ml ethidium bromide is previously added to the gel. Electrophoresis was regarded as complete when the number and intensity of the bands for DNA fragments no longer changed.

The enzyme activity which ensures complete decomposition of 1 μg λ-DNA after one hour's reaction at 37° C. was defined as one unit.

The restriction enzyme of this invention has the properties as described below.

(1) Action and substrate specificity

This endonuclease is capable of recognizing and cleaving the base sequence as shown below on a double-stranded DNA molecule, and is an isoschizomer of the known endonucleases Sac II and Sst II,

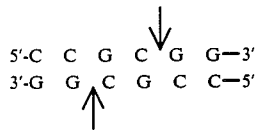

The recognition sequence of this enzyme was determined by using λ-DNA, pBR322 DNA and φ×174 RFI DNA (products of Takara Shuzo Co., Ltd.), as well as adenovirus type-2 DNA (product of Bethesda Research Laboratories) as substrate. It was found that this enzyme cleaves λ-DNA at four sites, φ 174 RFI DNA at one site, and adenovirus type-2 DNA at more than 25 sites, but has no action upon pBR322 DNA. In addition, the known restriction endonuclease Sac II was allowed to act upon these substrates. The cleavage patterns thus obtained were identical to those with the restriction enzyme of this invention. Based on these findings, it was concluded that the nucleotide sequence the present endonuclease can recognize is 5'-CCGCGG-3'.

Two methods were used to determine the positions of cleavage by restriction endonuclease of this invention: determining the 5'-terminal base of fragments obtained when adenovirus type-2 DNA is cleaved with the present endonuclease; and synthesis of an oligonucleotide carrying the recognition sequence of this enzyme, action of the present endonuclease, and determining the chain length of resulting fragments. The experimental procedure is detailed below.

Adenovirus type-2 DNA was completely digested with a preparation of this enzyme, followed by treatment with alkaline phosphatase (Takara Shuzo Co., Ltd.) to remove terminal phosphoric acids from DNA fragments. Radioactive phosphoric acid was then attached to the terminals of the DNA fragments by using polynucleotide kinase (Takara Shuzo Co., Ltd.) and [γ-$^{32}$P]ATP, the phosphates thus formed were digested by the action of P1 nuclease (Yamasa Shoyu Co., Ltd.) down to mononucleotides, and the decomposed products were analyzed on a PEI-cellulose thin-layer plate (Masherey and Nagel Co.). The labelled 5'-mononucleotide that was detected by this test was guanosine.

Separately, oligonucleotide d (GACCGCGGTC), which is self-complementary in nature, was synthesized by the solid phase method, the 5'-terminals were labelled with polynucleotide kinase and [γ-$^{32}$P]ATP, and the oligonucleotides were annealed into a double-stranded DNA. This was cleaved with this enzyme, and the reaction products were analyzed on a DEAE-cellulose thin-layer plate (Masherey and Nagel Co.), giving labelled spots for hexanucleotide, 5'-GACCGC.

Based on the results obtained above, it was concluded that the endonuclease of this invention recognizes the base sequence as shown below and cleaves the DNA at the arrow-marked positions,

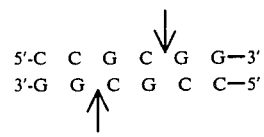

(2) Optimal conditions for enzymatic activity (a) Optimal temperature

The optimal temperature for this enzyme is about 37° C.

(b) Optimal pH

The optimal pH for this enzyme is in the range from 7.5 to 8.5.

(c) Salt concentration

The activity is maintained at NaCl and KCl concentrations up to 40 mM, but is inhibited at higher levels.

(d) MgCl$_2$ concentration

The enzyme is kept active in the presence of 5 to 20 mM MgCl$_2$.

The following Examples further illustrate this invention but are not intended to limit its scope.

EXAMPLE 1

A culture medium (160 liters) of the composition shown in Table 2 below was charged in a 200-liter jar fermentor and sterilized in a usual way.

Glucobacter albidus IFO 3251 was propagated in a medium of the same composition as above at 26° C. for 36 hours by the shake culture method, the inoculum thus obtained (3 liters) was inoculated to the culture medium in the jar fermentor, and cultivation was continued at 26° C. for 18 hours under agitation (250 rpm) and aeration (1 vvm). The grown cells were collected by a refrigerated centrifuge (wet yield: about 640 grams from 160 liters of culture medium).

TABLE 2

| | |
|---|---|
| Glucose | 5 g |
| Glycerol | 15 ml |
| Yeast extract | 5 g |
| Polypeptone | 5 g |
| KH$_2$PO$_4$ | 0.5 g |
| K$_2$HPO$_4$ | 0.5 g |
| Deionized water | 1 l |
| pH | 6.5 |

The microbial cells (200 g) were dispersed in 1000 ml of an extractive buffer (20 mM Tris-HCl, pH: 7.5, 10 mM 2-mercaptoethanol), the dispersion was subjected to ultrasonic treatment to disrupt the cell walls, and the resulting mixture was centrifuged for one hour (at 100,000×g) to remove the residue.

To the extract of enzyme thus obtained was added ammonium sulfate to 80% saturation, the precipitate which separated out was collected by centrifugation and dissolved in a buffer solution A (10 mM potassium phosphate buffer, pH: 7.5, 10 mM 2-mercaptoethanol, 5% glycerol), and the solution was dialyzed overnight against buffer A.

The dialyzate was adsorbed on DEAE-cellulose (Whatman Co., DE52), which was packed in a 65×95 mm column and equilibrated with buffer A, the column was washed with buffer A, and the adsorbed portion was eluted with buffer A containing KCl (linear concentration gradient from 0 to 0.6M). Activity of this enzyme was detected in fractions of 0.15 to 0.23M KCl concentration.

These active fractions were joined together, the combined solution was dialyzed overnight against buffer A, and the dialyzate was adsorbed on Affi-Gel Blue agarose (product of Bio-Rad Laboratories, 100 to 200 mesh) which was packed in a 25×100 mm column and equilibrated with buffer A. After washing with buffer A, the adsorbed portion was eluted with buffer A containing KCl (linear concentration gradient from 0 to 1.0M). Activity of this enzyme was detected in fractions of 0.44 to 0.66M KCl concentration.

These active fractions were collected together, the combined solution was dialyzed overnight against a buffer solution B (20 mM potassium phosphate buffer, pH: 7.5, 10 mM 2-mercaptoethanol, 10% glycerol), and the dialyzate was adsorbed on heparin-Sepharose (Pharmacia Fine Chemicals, CL-6B) packed in a 10×130 mm column and equilibrated with buffer B. After washing with buffer B, the adsorbed portion was eluted with buffer B containing KCl (linear concentration gradient from 0 to 0.8M). Activity of this enzyme was detected in fractions of 0.20 to 0.26M KCl concentration.

The active fractions were joined together, and the combined solution was dialyzed overnight against buffer B. The dialyzate was then adsorbed on heparin-Sepharose (Pharmaica Fine Chemicals, CL-6B) packed in a 5×50 mm column and equilibrated with buffer B. After washing with buffer B, the adsorbed portion was eluted with buffer B containing 0.5M KCl, giving a preparation of this enzyme.

This preparation contained no non-specific nuclease nor phosphatase.

Thus 75,000 units of this enzyme was obtained from 200 g of wet microbial cells.

As is apparent from the foregoing, this invention provides an advantageous method for producing a endonuclease having the same recognition sequence and cleavage positions as Sac II and Sst II on an industrial basis.

What we claim is:

1. A process for producing a restriction endonuclease capable of recognizing the nucleotide sequence as shown below on a DNA chain and specifically cleaving the double-stranded chain at the arrow-marked positions, which comprises growing a microorganism belonging to the genus Gluconobacter and capable of producing said restriction endonuclease, and collecting the enzyme thus formed from the culture broth,

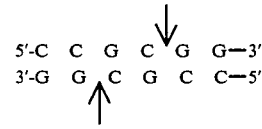

(wherein C represents cytidine, and G guanosine).

* * * * *